(12) United States Patent
Raijman et al.

(10) Patent No.: US 7,632,241 B2
(45) Date of Patent: Dec. 15, 2009

(54) MULTI-LUMEN BILIARY CATHETER WITH ANGLED GUIDEWIRE EXIT

(75) Inventors: Isaac Raijman, Bell Arie, TX (US); John E. Dimitriou, Stow, MA (US)

(73) Assignee: Conmed Endoscopic Technologies, Inc., Utica, NY (US)

( * ) Notice: Subject to any disclaimer, the term of this patent is extended or adjusted under 35 U.S.C. 154(b) by 546 days.

(21) Appl. No.: 10/275,540

(22) PCT Filed: May 17, 2001

(86) PCT No.: PCT/US01/15974

§ 371 (c)(1),
(2), (4) Date: Jun. 5, 2003

(87) PCT Pub. No.: WO01/89603

PCT Pub. Date: Nov. 29, 2001

(65) Prior Publication Data

US 2004/0064128 A1 Apr. 1, 2004

Related U.S. Application Data

(60) Provisional application No. 60/206,012, filed on May 19, 2000.

(51) Int. Cl.
*A61M 3/00* (2006.01)
(52) U.S. Cl. ...................................................... 604/43
(58) Field of Classification Search .................. 604/523, 604/524, 525, 100.01, 100.02, 164.13, 173, 604/264, 43
See application file for complete search history.

(56) References Cited

U.S. PATENT DOCUMENTS

| 3,105,492 A | | 10/1963 | Jeckel |
| 4,307,723 A | | 12/1981 | Finney |
| 4,364,394 A | * | 12/1982 | Wilkinson ............. 604/102.02 |
| 4,464,175 A | * | 8/1984 | Altman et al. ............ 604/99.01 |
| 4,531,933 A | | 7/1985 | Norton et al. |
| 4,699,611 A | | 10/1987 | Bowden |
| 4,769,005 A | | 9/1988 | Ginsburg et al. |
| 4,894,057 A | * | 1/1990 | Howes ........................ 604/523 |

(Continued)

FOREIGN PATENT DOCUMENTS

EP 0451966 B1 6/1994

(Continued)

OTHER PUBLICATIONS

Venu et al., "A new guidewire technique for biliary strictures" *Gastrointestinal Endoscopy* 37:553-555 (1991).

(Continued)

*Primary Examiner*—Christopher Koharski
(74) *Attorney, Agent, or Firm*—Marjama Muldoon Blasiak & Sullivan LLP

(57) ABSTRACT

A multi-lumen biliary catheter in which at least one of the lumens (14, 16) has a side opening port (24, 26) configured to guide a guidewire (32) out of that port at an angle to the longitudinal axis of the catheter. Radiopaque marker bands (34) having different lengths are placed on the distal end of the catheter adjacent the distal openings to facilitate fluoroscopic identification of the distal end orientation in the biliary tract.

20 Claims, 5 Drawing Sheets

U.S. PATENT DOCUMENTS

| | | | | |
|---|---|---|---|---|
| 4,898,591 | A | * | 2/1990 | Jang et al. .................. 604/527 |
| 4,955,859 | A | | 9/1990 | Zilber |
| 5,059,177 | A | | 10/1991 | Towne et al. |
| 5,116,310 | A | * | 5/1992 | Seder et al. .................. 604/43 |
| 5,129,910 | A | | 7/1992 | Phan et al. |
| 5,221,256 | A | * | 6/1993 | Mahurkar .................. 604/43 |
| 5,609,624 | A | | 3/1997 | Kalis |
| 5,910,170 | A | | 6/1999 | Reimink et al. |
| 5,916,194 | A | | 6/1999 | Jacobsen et al. |
| 5,944,712 | A | * | 8/1999 | Frassica et al. ............. 604/529 |
| 5,984,965 | A | | 11/1999 | Knapp et al. |
| 6,019,786 | A | | 2/2000 | Thompson |
| 6,099,513 | A | * | 8/2000 | Spehalski .................. 604/264 |
| 6,206,849 | B1 | * | 3/2001 | Martin et al. ................. 604/43 |
| 6,231,563 | B1 | | 5/2001 | White et al. |

FOREIGN PATENT DOCUMENTS

| | | |
|---|---|---|
| WO | WO 00/18322 | 4/2000 |
| WO | WO 01/89419 | 5/2001 |

OTHER PUBLICATIONS

COOK® Wilson-Cook Medical GI Endoscopy, On-Line Company Brochure (1999).

U.S. Appl. No. 10/275,498, filed Jun. 5, 2003, Raijman.

U.S. Appl. No. 10/867,428, filed Jul. 14, 2004, Aznoian.

* cited by examiner

MULTI-LUMEN BILIARY CATHETER WITH ANGLED GUIDEWIRE EXIT

CROSS-REFERENCE TO RELATED APPLICATIONS

This is a regular utility application that claims the benefit of U.S. Provisional Application No. 60/206,012, filed May 19, 2000 the contents of which are incorporated herein by reference.

FIELD OF THE INVENTION

This invention relates to catheters and guidewires adapted for use in luminal systems of a human body. More specifically, the invention is adapted for use in the biliary tract.

BACKGROUND OF THE INVENTION

Among the procedures involved in diagnosis and treatment of medical conditions involving the biliary tract are those that require the use of a guidewire in order to facilitate advancement of a selected catheter to a selected site in the biliary tract. Typically, such procedures are performed through the working channel of an endoscope. Such procedures include ERCP in which radiopaque contrast liquid is injected into portions of the biliary tract to enable the physician to visualize the anatomy of the tract as an aid in diagnosis. Among the procedures that may be performed are those relating to treatment of an obstructed duct, as may result from tumors, gall stones or other medical conditions. Procedures may be employed to dilate the obstructed region, as with a dilatation catheter, or to remove stones, among others. It has become increasingly common to place a stent in the duct so that after the obstruction in the duct has been treated to restore patency, the stent maintains that patency. Additionally, the physician may wish to place multiple stents in the region of the branched portions of the biliary tract, even if the adjacent portion of the duct has not been and does not need treatment at the time. The decision to place a stent in each of adjacent branches may be prompted by the difficulty in accessing the second branch with a guidewire after a stent has been placed in the first branch. It has been found that after a stent has been placed in one branch of the tract in proximity to the juncture of the branches, considerable difficulty can be expected in trying to place a second guidewire in the other branch. Consequently, it may be preferable to place both stents at the same time. The present invention facilitates such placement as well as provides a versatile catheter usable in other techniques associated with the biliary tract.

SUMMARY OF THE INVENTION

The advantages of the invention are achieved with a multi-lumen catheter, preferably having three lumens, in which at least one, and preferably two of the lumens, have distal outlets that are oriented to direct a guidewire out of those lumens along a direction that is angled with respect to the longitudinal axis of the catheter. One of the lumens in the catheter extends fully to the distal tip of the catheter and defines a distally facing outlet at the distal tip. Although any of the lumens can be used for the placement of guidewires or for the injection of contrast media, the lumen(s) with the angled exit port(s) is particularly useful in a number of situations involving guidewire placement. For example, should it be difficult to place a guidewire in a biliary branch with the lumen having the distally facing outlet, the catheter can be adjusted by longitudinal displacement to align an angled guidewire exit port with the entrance to that branch, thereby providing a direct alignment between the exit port and the biliary branch so that the guidewire can be aligned and advanced directly into the branch. Additionally, the invention is useful in facilitating placement of two guidewires in a pair of branches and then removing the catheter, leaving the two guidewires in place. With the guidewires having been so placed, each can serve as a guide for a stent delivery catheter. By placing both guidewires in the adjacent biliary branches before placement of either stent, it will be possible to achieve easy access to both branches, even after a stent has been placed in one of the branches.

It is among the general objects of the invention to provide a multi-lumen biliary catheter that has a high degree of versatility in that each of the lumens of the catheter may be used either for placement of a guidewire or for transmission of liquids or media between the duct and the proximal end of the catheter. Also among the objects of the invention is to provide a multi-lumen biliary catheter in which at least one, and preferably two of the lumens, has an angled exit port at its distal end configured to direct a guidewire exiting through the port to be directed at an angle to the longitudinal axis of the catheter; to provide a technique by which a plurality of guidewires can be placed within the biliary tract to serve in readiness for advancement of catheters selectively and independently along one or more of those guidewires; and to provide a catheter that facilitates placement of a guidewire in an angled branch of the biliary tree.

DESCRIPTION OF THE DRAWINGS

The foregoing and other objects and advantages of the invention will be appreciated more fully from the following further description thereof, with reference to the accompanying drawings wherein.

DETAILED DESCRIPTION

Figure 2:
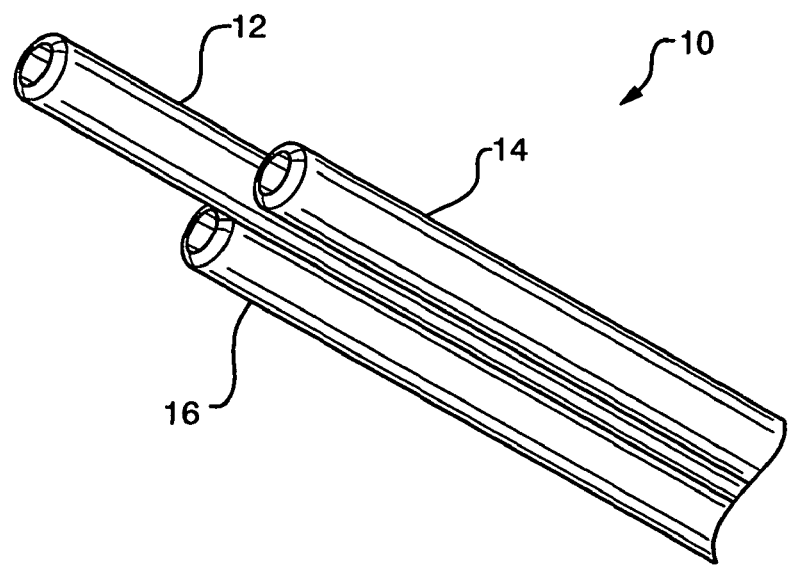
FIG. 2 is an illustration in perspective of a three-lumen tube that may be used to fabricate a catheter in accordance with the invention.
Figure 3:
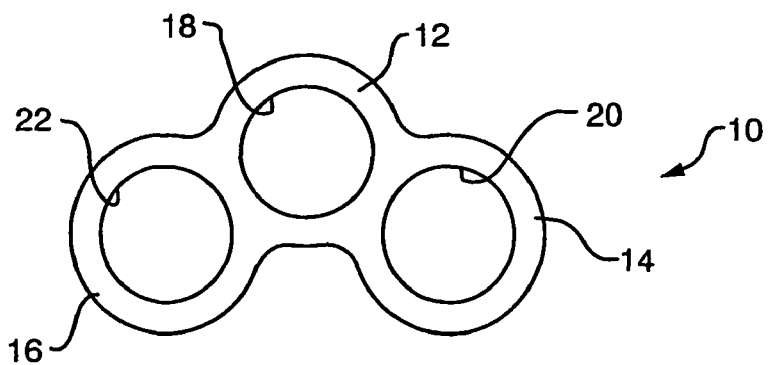
FIG. 3 is a cross-sectional diagram of a preferred embodiment of a three-lumen catheter embodying the invention.

FIGS. 2 and 3 illustrate the preferred configuration of an extruded polymeric tube having three lumens. The cross section of the extruded tube, indicated generally at 10, includes what may be considered as a central tube 12 and a pair of side tubes 14, 16. The side tubes 14, 16 may be formed as a unitary structure with the central tube 12 during the extrusion process. Preferably the extrusion is formed from a polyether block amide block co-polymer commercially available under the trade designation PEBAX®. A number of PEBAX grades, or blends of PEBAX grades, can be used to achieve the desired shaft stiffness. A preferred grade of the block co-polymer is PEBAX 7033. As shown, the maximum transverse dimension of the catheter shaft in this embodiment may be about 0.144 inches to allow advancement through a 3.8 mm working channel of an endoscope. Preferably, the transverse dimension of the catheter shaft is maintained at about 0.140 inches to be compatible with endoscopes having either 3.7 mm or 3.8 mm working channels.

Each of the tubes 12, 14, 16 defines a lumen, 18, 20, 22, respectively. It may be noted that although the three lumens 18, 20, 22 could be placed closer together in a more compact pattern, for example, if the catheter were circular in outer cross section, it is considered desirable that the side lumens 20, 22 do not lie closely adjacent each other. Thus, it is preferred that the centers of the side lumens are spaced from each other a distance greater than that between the central lumen 18 and each of the side lumens 20, 22. Viewed another way, the centers of the lumens may be considered as defining an isosceles, but not equilateral, triangle in which a line between the centers of the side lumens 20, 22 would define the hypotenuse. The relative angular orientation of the lumens 18, 20, 22 is as illustrated in FIG. 3.

Figure 1A:
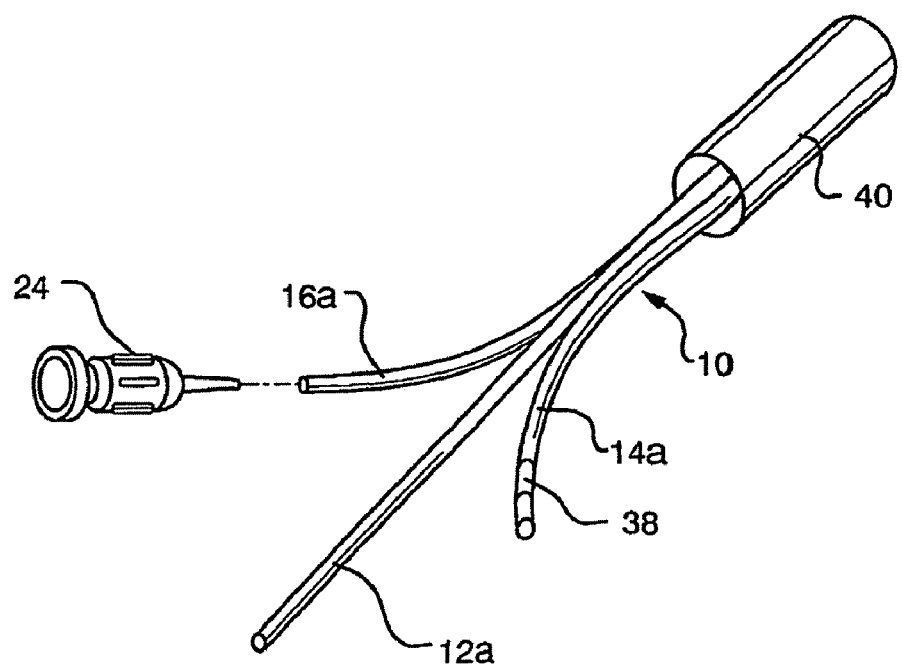
FIG. 1A is a diagrammatic illustration of the proximal end of a three-lumen catheter embodying the invention, showing the proximal end in partial stages of manufacture.
Figure 1B:
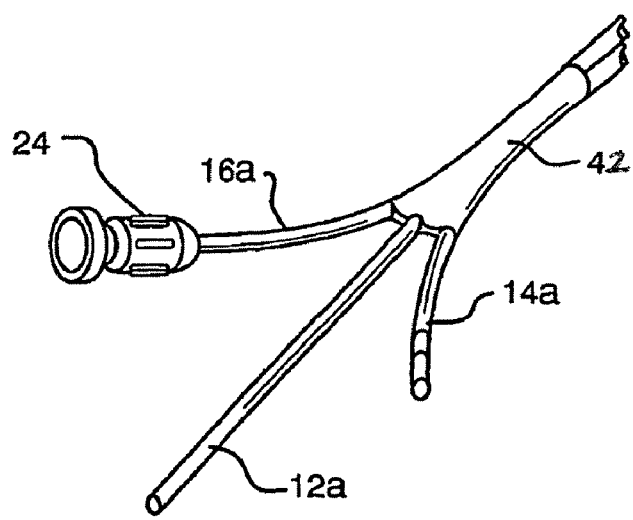
FIG. 1B is a diagrammatic illustration of the proximal end of a three-lumen catheter according to one embodiment of the invention.

The proximal end of the catheter may be formed in the manner suggested in FIGS. 1A and 1B in which a length of the extrusion is separated longitudinally to define three separate tubes 12a, 14a and 16a. A luer fitting 24 may be secured to the proximal end of each of the tubes 12a, 14a and 16a, only one of which is shown in FIG. 1 for clarity of illustration. By providing luer fittings at the proximal end of each of the tubes, each of the lumens, 18, 20, 22 can be used selectively for a guidewire or for fluid flow functions. The proximal tubes 12a, 14a and 16a may be bound together by shrink tubing 40 (FIG. 1A), or by molding a proximal trifurcation 42 (FIG. 1B). The center tube 12a preferably is longer than the side tubes 14a, 16a. One of the side legs, such as side leg 14a shown in FIGS. 1A and 1B, may be provided with a visual marker 38 at the proximal end. The importance of the visual marker with respect to the distal end of the catheter is explained below.

Figure 4:
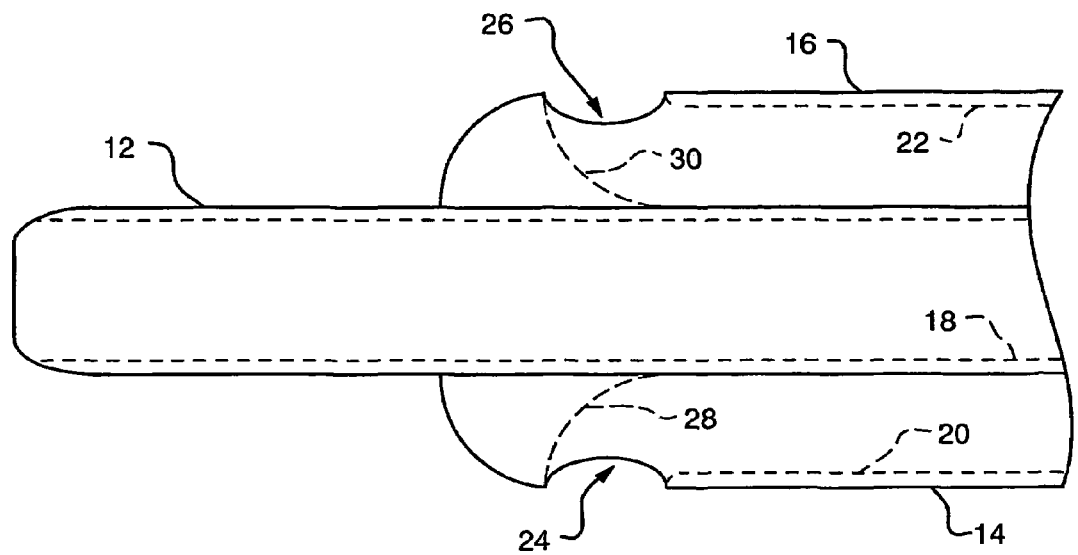
FIG. 4 is an enlarged cross-sectional plan view of a three-lumen embodiment of the invention illustrating the configuration of the exit ramps at the distal ends of two of the lumens
Figure 5:
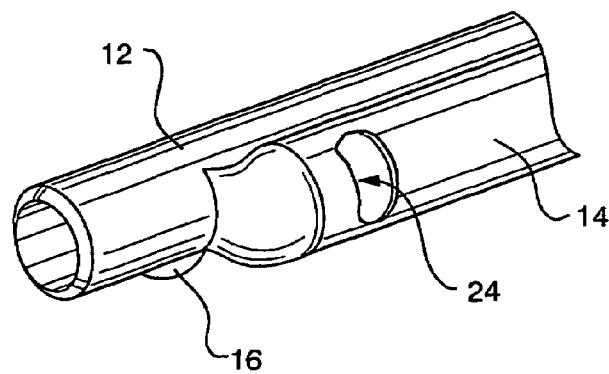
FIG. 5 is a somewhat diagrammatic isometric illustration of the distal end of the invention.
Figure 6A:
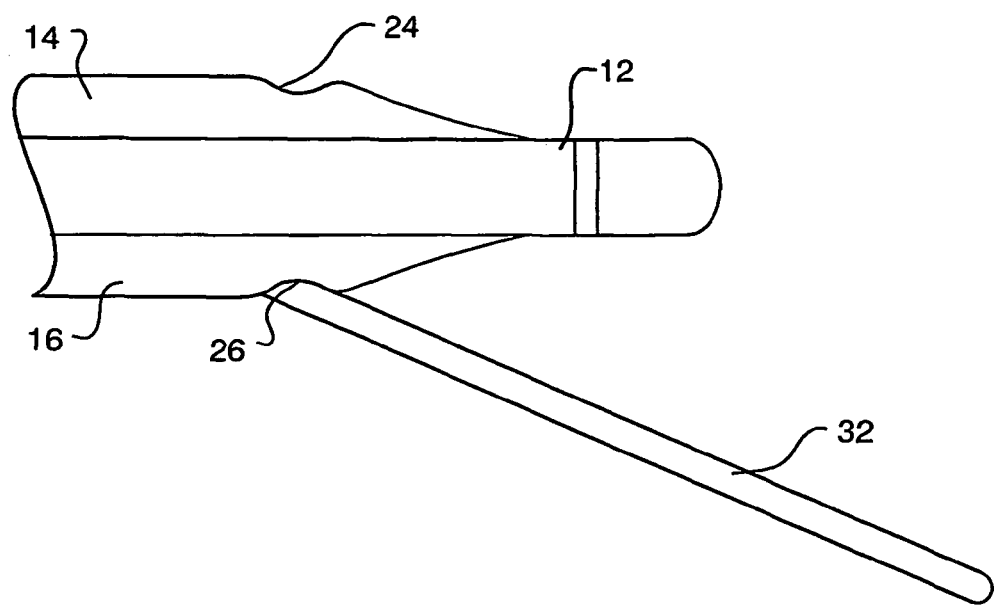
FIG 6A is a somewhat diagrammatic illustration of the distal end of a three lumen catheter embodying the invention showing a guidewire projecting at an angle from one of the lumens.

The distal end of the catheter is formed by first trimming the distal ends of the side tubes 14, 16 so that a length of the central tube 12 projects distally beyond the ends of the side tubes 14, 16. FIG. 2 illustrates the approximate relative lengths of the tubes 12, 14, and 16, although it should be understood that the relative lengths of the distal end of the device may be varied. The distal ends of the side tubes 14, 16 are worked, as by heating and molding, so that at least one, and preferably both, terminate in an angled exit port 24, 26, as indicated in FIGS. 4 and 5. The angled ports 24, 26 may be formed by placing a suitably oriented mandrel in the distal portion of the lumens 20, 22 and then melting and filling the thermoplastic PEBAX or other suitable polymer to close off the distal opening of the tubes while forming the side openings 24, 26 with angled ramps 28, 30 that will guide the distal ends of the guidewires out at a desired angle of emergence with respect to the longitudinal axis of the catheter. FIG. 6A illustrates a guidewire extended through the lumen of side tube 16 with the guidewire 32 projecting out of the angled port 26 at the selected angle of emergence.

Figure 7:
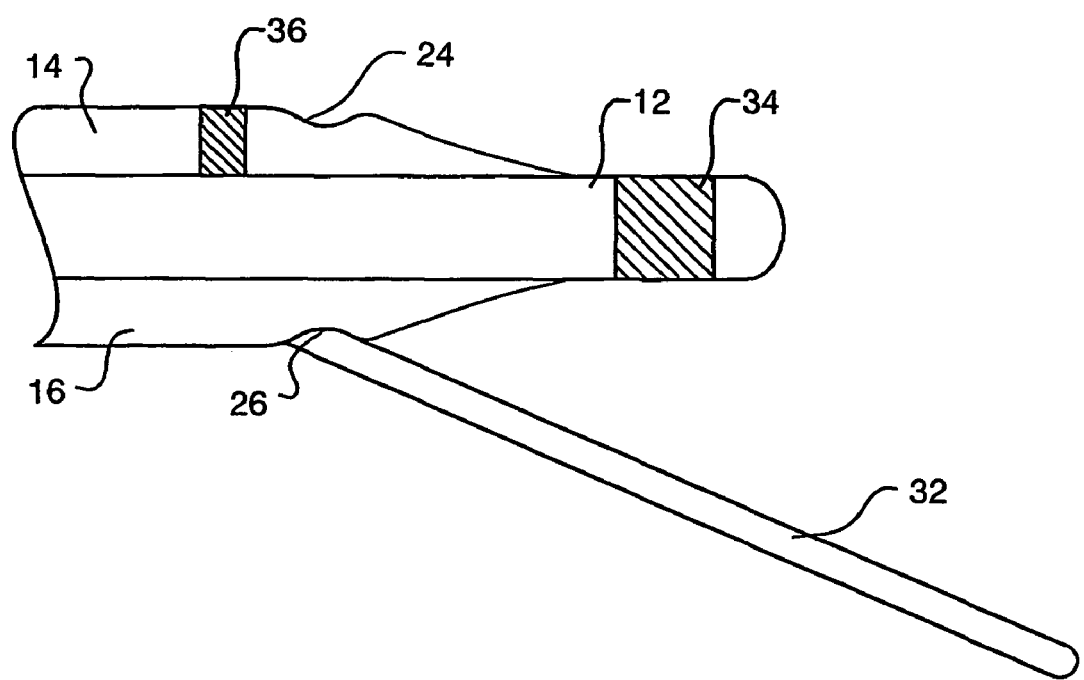
FIG. 7 is a diagrammatic illustration of the distal end of a three-lumen catheter with radiopaque markers having different lengths.

To facilitate orientation of the distal end when the catheter is in use, a relatively long radiopaque marker band 34 (shown in FIG. 7) is secured to or formed on the distal end of central tube 12 and a relatively shorter radiopaque marker band 36 (FIG. 7) is secured to or formed on the distal end of side tube 14. Radiopaque marker band 36 corresponds with visual marker band 38 on leg 14a (FIG. 1A). The use of different lengths of radiopaque marker bands at the distal end of the catheter provides a means to fluoroscopically ascertain the orientation of the catheter end relative to the anatomy of the biliary tract or any other tract being evaluated. By having only one side tube labeled with a radiopaque marker at its distal end and having a corresponding visual marker at its proximal end, the user can distinguish between the two side tubes and selectively insert a guidewire or inject contrast media or other fluid into the desired side tube.

Figure 6B:
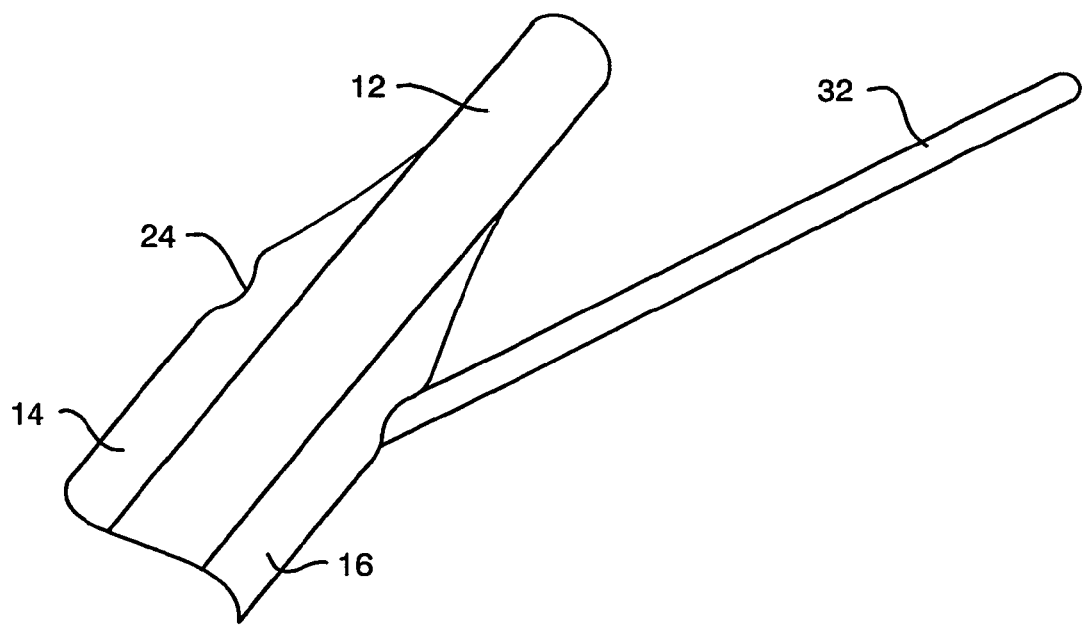
FIG. 6B is an illustration similar to FIG. 6A showing a guidewire projecting at an angle of emergence of about 25° from the other lumen.

FIG. 6B is similar to FIG. 6A except that it includes preferred dimensional details of the distal tip of the device as well as indicates an angle of emergence of about 25°. From FIG. 6B it will be appreciated that if the catheter were to be advanced and could not itself be directed into a desired branch, the catheter could be manipulated longitudinally to orient the exit port 26 with the entry to that angled branch. The ramps 24, 26 should be configured to provide a smooth engagement of the distal end of the guidewire with the ramps to assure that the distal end of the guidewire will not become snagged at the exit ports. Additionally, it should be appreciated that although an emerging angle of about 25° is illustrated as being preferred, that angle may be varied within reasonably acceptable limits including from about 1° to about 45°.

The invention is versatile in that it can be used in a number of different modes. In the preferred embodiment, all of the lumens are the same diameter and can be used with equal facility to receive a guidewire or to communicate fluids between its proximal and distal ends. The catheter may be used as a canulating catheter to advance through the papilla into the biliary tract. It may be used to provide access to a branch duct that cannot otherwise be accessed by aligning an exit port of a side lumen with the entry to that branch and then advancing a guidewire through the catheter so that it emerges from that exit port and passes directly into the desired branch. Moreover, when it is desired to place a stent in a biliary branch, the invention enables stent placement to be preceded by placing of two guidewires, one in each of the two branches, so that after the first stent has been placed, the second branch will already have been accessed by a second guidewire, thereby facilitating access of the stent delivery catheter into the second branch. Although the catheter has been described with respect to its application to the biliary tree, it should be understood that the relative configuration of the tubes and their respective distal ends can be used to facilitate advancement of guidewires or fluids into selected branches of any branching system of a mammalian body and in particular, a human body.

It should be understood that the foregoing description of the invention is intended merely to be illustrative thereof and that other modifications, embodiments and equivalence may be apparent to those skilled in the art without departing from its principles.

The invention claimed is:

1. A catheter comprising a shaft extending in a proximal direction from a shaft distal end to a shaft proximal end along a longitudinal axis, the shaft comprising:
   a first tubular member defining a first lumen, the first lumen comprising (i) a first exit port and (ii) a first lumen longitudinal portion extending in the proximal direction away from the first exit port, wherein the first lumen longitudinal portion has a center as viewed in a cross section perpendicular to the longitudinal axis;

a second tubular member defining a second lumen, the second lumen comprising (i) a second lumen exit port having an axis that forms an angle with the longitudinal axis, (ii) a second lumen longitudinal portion extending in the proximal direction away from the second lumen exit port and extending parallel to the longitudinal axis, and (iii) a second lumen ramp portion extending in the proximal direction between the second lumen exit port and the second lumen longitudinal portion, so as to smoothly engage a distal end of a second lumen guidewire and avoid a snagging of the distal end of the second lumen guidewire at the second lumen exit port, and wherein the second lumen longitudinal portion has a center as viewed in the cross section perpendicular to the longitudinal axis; and a third tubular member defining a third lumen, the third lumen comprising (i) a third lumen exit port having an axis that forms an angle with the longitudinal axis, (ii) a third lumen longitudinal portion extending in the proximal direction away from the third lumen exit port and extending parallel to the longitudinal axis, and (iii) a third lumen ramp portion extending in the proximal direction between the third lumen exit port and the third lumen longitudinal portion so as to smoothly engage a distal end of a third lumen guidewire and avoid a snagging of the distal end of the third lumen guidewire at the third lumen exit port, and wherein the third lumen longitudinal portion has a center as viewed in the cross section perpendicular to the longitudinal axis;

wherein the first lumen extends distally beyond a distal end of the second lumen, wherein a first imaginary line connecting the center of the second lumen longitudinal portion and the center of the third lumen longitudinal portion is longer than each of a second imaginary line connecting the center of the first lumen longitudinal portion to the center of the second lumen longitudinal portion and a third imaginary line connecting the center of the first lumen longitudinal portion to the center of the third lumen longitudinal portion, and wherein a first outer cross sectional thickness of the shaft measured along a line arranged perpendicular to the first imaginary line is less than a second outer cross sectional thickness of the shaft measured parallel to the first imaginary line.

2. A catheter as defined in claim 1, wherein each of the second lumen longitudinal portion and the third lumen longitudinal portion have a circular cross section as viewed in the cross section perpendicular to the longitudinal axis.

3. A catheter as defined in claim 1 further comprising (i) a first radiopaque marker band having a first length on a distal end of the first tubular member, (ii) a second radiopaque marker band having a second length on a distal end of the second tubular member, and (iii) no radiopaque marker on the third tubular member.

4. A catheter as defined in claim 3 further comprising a visual marker on a proximal end of the second tubular member.

5. A catheter as defined in claim 1, wherein the second outer cross sectional thickness of the shaft is less than or equal to about 0.144 inches to allow advancement through a 3.8 mm working channel of an endoscope.

6. A catheter as defined in claim 1, wherein a base wall of the second lumen ramp portion and a distal edge of the second lumen exit port define a second guidewire angle of emergence from about 1° to 45° from the longitudinal axis.

7. A catheter as defined in claim 6, wherein a base wall of the third lumen ramp portion and a distal edge of the third lumen exit port define a third guidewire angle of emergence from about 1° to 45° from the longitudinal axis.

8. A catheter as defined in claim 1 further comprising a shrink tube encircling the first tubular, the second tubular member, and the third tubular member along a portion of the shaft.

9. A catheter as defined in claim 1 wherein the shaft is formed of a block co-polymer.

10. A catheter as defined in claim 9, wherein the block co-polymer is a grade or a blend of grades of polyether block amides.

11. A catheter comprising a shaft extending in a proximal direction from a shaft distal end to a shaft proximal end along a longitudinal axis, the shaft comprising:

a first tubular member defining a first lumen, the first lumen comprising (i) a first exit port and (ii) a first lumen longitudinal portion extending in the proximal direction away from the first exit port and extending parallel to the longitudinal axis, wherein the first lumen longitudinal portion has a center as viewed in a cross section perpendicular to the longitudinal axis;

a second tubular member defining a second lumen, the second lumen comprising (i) a second lumen exit port having an axis that forms an angle with the longitudinal axis, (ii) a second lumen longitudinal portion extending in the proximal direction away from the second exit port and extending parallel to the longitudinal axis, and (iii) a second lumen ramp portion extending between the second lumen exit port and the second lumen longitudinal portion, wherein a base wall of the second lumen ramp portion, as viewed in a cross section bisecting the second lumen exit port and extending along a center longitudinal axis of the of the second lumen longitudinal portion, extends in the proximal direction from a distal edge of the second lumen exit port to the second lumen longitudinal section so as to smoothly engage a distal end of a second lumen guidewire and avoid a snagging of the distal end of the second lumen guidewire at the second lumen exit port, wherein the second lumen longitudinal portion has a center as viewed in the cross section perpendicular to the longitudinal axis; and a third tubular member defining a third lumen, the third lumen comprising (i) a third lumen exit port having an axis that forms an angle with the longitudinal axis, (ii) a third lumen longitudinal portion extending in the proximal direction from the third lumen exit port and parallel to the longitudinal axis, and (iii) a third lumen ramp portion extending between the third lumen exit port and the third lumen longitudinal portion, wherein a base wall of the third lumen ramp portion, as viewed in a cross section bisecting the third lumen exit port and extending along a center longitudinal axis of the third lumen longitudinal portion, extends in the proximal direction from a distal edge of the third lumen exit port and the third lumen longitudinal portion so as to smoothly engage a distal end of a third lumen guidewire and avoid a snagging of the distal end of the third lumen guidewire at the third lumen exit port, wherein the third lumen longitudinal portion has a center as viewed in the cross section perpendicular to the longitudinal axis;

wherein the first lumen extends distally beyond a distal end of the second lumen, wherein a first imaginary line connecting the center of the second lumen longitudinal portion and the center of the third lumen longitudinal portion is longer than each of a second imaginary line connecting the center of the first lumen longitudinal portion to the center of the second lumen longitudinal portion and a third imaginary line connecting the center of the first lumen longitudinal portion to the center of the third lumen longitudinal portion, and wherein a first outer cross sectional thickness of the shaft measured along a line arranged perpendicular to the first imaginary line is less than a second outer cross sectional thickness of the shaft measured parallel to the first imaginary line.

12. A catheter as defined in claim 11, wherein each of the second lumen longitudinal portion and the third lumen longitudinal portion have a circular cross section as viewed in the cross section perpendicular to the longitudinal axis.

13. A catheter as defined in claim 11 further comprising (i) a first radiopaque marker band having a first length on a distal end of the first tubular member, (ii) a second radiopaque marker band having a second length on a distal end of the second tubular member, and (iii) no radiopaque marker on the third tubular member.

14. A catheter as defined in claim 13 further comprising a visual marker on a proximal end of the second tubular member.

15. A catheter as defined in claim 11, wherein the second outer cross sectional thickness of the shaft is less than or equal to about 0.144 inches to allow advancement through a 3.8 mm working channel of an endoscope.

16. A catheter as defined in claim 11, wherein a base wall of the second lumen ramp portion and a distal edge of the second lumen exit port define a second guidewire angle of emergence from about 1° to 45° from the longitudinal axis.

17. A catheter as defined in claim 16, wherein a base wall of the third lumen ramp portion and a distal edge of the third lumen exit port define a third guidewire angle of emergence from about 1° to 45° from the longitudinal axis.

18. A catheter as defined in claim 11 further comprising a shrink tube encircling the first tubular, the second tubular member, and the third tubular member along a portion of the shaft.

19. A catheter as defined in claim 11, wherein the shaft is formed of a block co-polymer.

20. A catheter as defined in claim 19, wherein the block co-polymer is a grade or a blend of grades of polyether block amides.

* * * * *